United States Patent [19]
Gates

[11] Patent Number: 5,683,446
[45] Date of Patent: Nov. 4, 1997

[54] MEDICAL ELECTRICAL LEAD HAVING AN ANCHORING SLEEVE RETAINING DEVICE

[75] Inventor: James T. Gates, Maple Grove, Minn.

[73] Assignee: Medtronic, Inc., Minneapolis, Minn.

[21] Appl. No.: 450,761

[22] Filed: May 25, 1995

[51] Int. Cl.$^6$ ........................................ A61N 1/05
[52] U.S. Cl. .................. 607/126; 607/149; 607/116; 128/642
[58] Field of Search .................. 607/126, 122, 607/123, 127, 128, 116, 149; 128/639, 642

[56] References Cited

U.S. PATENT DOCUMENTS

| | | | |
|---|---|---|---|
| 3,598,118 | 8/1971 | Warren | 128/214.4 |
| 4,300,553 | 11/1981 | Seberg | 128/214.4 |
| 4,437,475 | 3/1984 | White | 128/785 |
| 4,553,961 | 11/1985 | Pohndorf et al. | 604/178 |
| 4,672,979 | 6/1987 | Pohndorf | 607/126 |
| 5,107,856 | 4/1992 | Kristiansen et al. | 607/126 |
| 5,242,431 | 9/1993 | Kristiansen | 607/126 |
| 5,258,015 | 11/1993 | Li et al. | 607/126 |

Primary Examiner—William E. Kamm
Assistant Examiner—Kennedy J. Schaetzle
Attorney, Agent, or Firm—Thomas F. Woods; Harold R. Patton

[57] ABSTRACT

The present invention is a transvenous lead having an anchoring sleeve retaining device. The transvenous lead features a lead covered by an insulative sleeve. Positioned at the distal end of the lead is an electrode assembly. Also positioned proximate the electrode assembly is a fixation mechanism. At the proximal end of the lead body is a terminal assembly. The terminal assembly permits the lead to be connected to a pulse generator. The anchoring sleeve retaining device further features a removable portion that frictionally engages the lead and prevents the anchoring sleeve from sliding along the lead prior to suturing the anchoring sleeve to the lead.

11 Claims, 3 Drawing Sheets

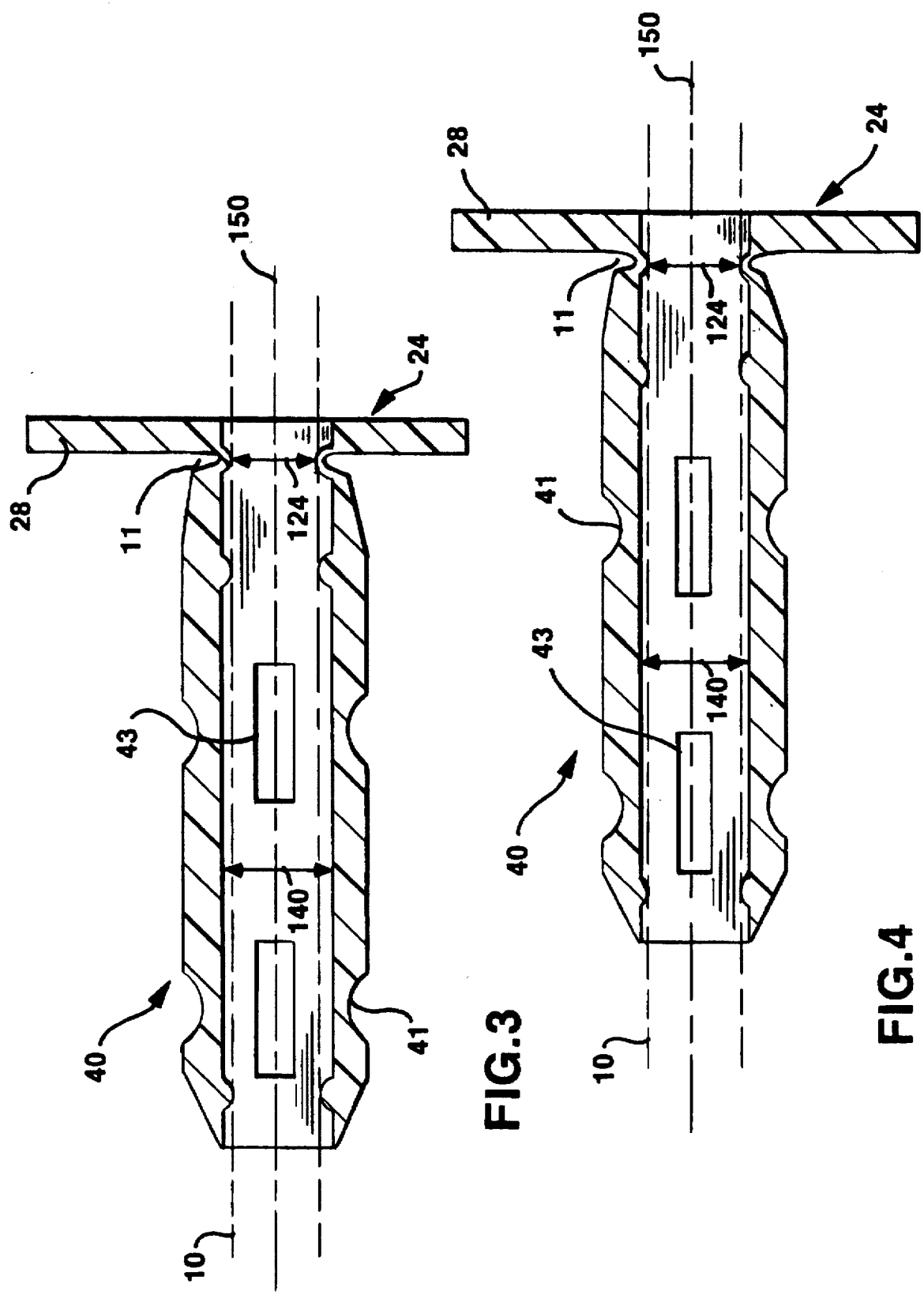

MEDICAL ELECTRICAL LEAD HAVING AN ANCHORING SLEEVE RETAINING DEVICE

FIELD OF THE INVENTION

This invention relates to the field of body implantable medical electrical leads, and in particular to a body implantable transvenous pacing lead which features an anchoring sleeve retaining device.

BACKGROUND OF THE INVENTION

In the medical field, various types of body implantable leads are known and used. One type of commonly used implantable lead is an endocardial pacing lead.

An endocardial pacing lead is attached at its proximal end to an implantable pulse generator and at its distal end to the endocardium of a cardiac chamber. The distal end of an endocardial lead may engage the endocardium by either an active fixation mechanism or a passive fixation mechanism.

Active fixation mechanisms use a structure such as a helix or hook to physically engage into or actively affix themselves onto the heart. Passive fixation mechanisms such as a tine assembly lodge or passively fix themselves to the heart.

A preferred means for introducing an endocardial lead into the heart is through a vein. A transvenous lead may be introduced into and maneuvered through the vein so the distal end is positioned within the heart. The lead must be secured in place at this remote location. Generally, an anchoring sleeve is permanently attached about the lead is employed to suture the proximal end of the lead to the tissue at the venous entry location. Newer leads may feature a design with a uniform diameter from the proximal end to the distal end of the lead, a so-called isodiametric design.

One difficulty which has been encountered with the newer isodiametric design, in particular, regards the anchoring sleeve. More particularly, the anchoring sleeve is mounted to slide along the lead. With the new isodiametric lead design it is possible for the anchoring sleeve to slip off the distal end of a lead with an active fixation mechanism or affix itself to the tines of a passive fixation mechanism. Moreover, it is also possible for the anchoring sleeve to slide along and cover a ring electrode of a bipolar pacing lead. This may affect the sensing performance of the implantable pulse generator, and should be avoided.

Finally, pre-implantation may also cause the anchoring sleeve to slip to the distal end of the lead. If not noticed by the implanting physician prior to final lead placement, the lead placement procedure will need to be repeated, and if not corrected may affect lead performance and ultimately affect the performance of the implantable pulse generator.

SUMMARY OF THE INVENTION

It is accordingly an object of the present invention to provide a transvenous lead which has an anchoring sleeve retaining device to prevent the anchoring sleeve from sliding off the distal end of an isodiametric lead.

This object is accomplished by providing a transvenous lead which has an anchoring sleeve retaining device. In particular, the transvenous lead of the present invention features a lead covered by an insulative sleeve. Positioned at the distal end of the lead is an electrode assembly. Also positioned proximate the electrode assembly is a fixation mechanism such as a tine or helix assembly. Positioned upon the proximal end of the lead is a terminal assembly.

The terminal assembly permits the lead to be connected to a pulse generator. Positioned proximate the terminal assembly about the lead is an anchoring sleeve retaining device. The anchoring sleeve retaining device is preferably made from an insulative bio-compatible material, preferably silicone. The anchoring sleeve retaining device further features a removable portion. The removable portion frictionally engages the lead and prevents the anchoring sleeve from sliding along the lead. In the preferred embodiment, a scored tear line aids in removing of the removable portion from the anchoring sleeve.

DETAILED DESCRIPTION OF THE DRAWINGS

FIG. 1 shows a side plan view of a transvenous pacing lead containing an anchoring sleeve retaining device;

FIG. 2 shows a side plan view of an anchoring sleeve retaining device shown in FIG. 1;

FIG. 3 shows a cross section of one embodiment of an anchoring sleeve of the present invention;

FIG. 4 shows a cross section of another embodiment of an anchoring sleeve of the present invention in conjunction with the anchoring sleeve retaining device shown in FIG. 2; and FIG. 5 shows a side plan view of a transvenous pacing lead with a passive fixation mechanism device.

The drawings are not necessarily to scale.

BRIEF DESCRIPTION OF THE DRAWINGS

The present invention is described in terms of an anchoring sleeve retaining device which may be employed on a transvenous pacing lead. The present invention, however, may be advantageously practiced in conjunction with many different types of implantable tranvenous pacing leads as well as diagnostic or therapeutic medical catheters. Thus, as used to describe the present invention, the term "lead" is used in the broadest sense and includes any elongated diagnostic or therapeutic medical device.

Terminal assembly 18 is provided at the proximal end of lead 10. Terminal assembly 18 is provided with sealing rings 20 and terminal pin 22 all of a type known in the art. Terminal assembly 18 permits lead 10 to be coupled to a pulse generator (not shown).

Figure 1:
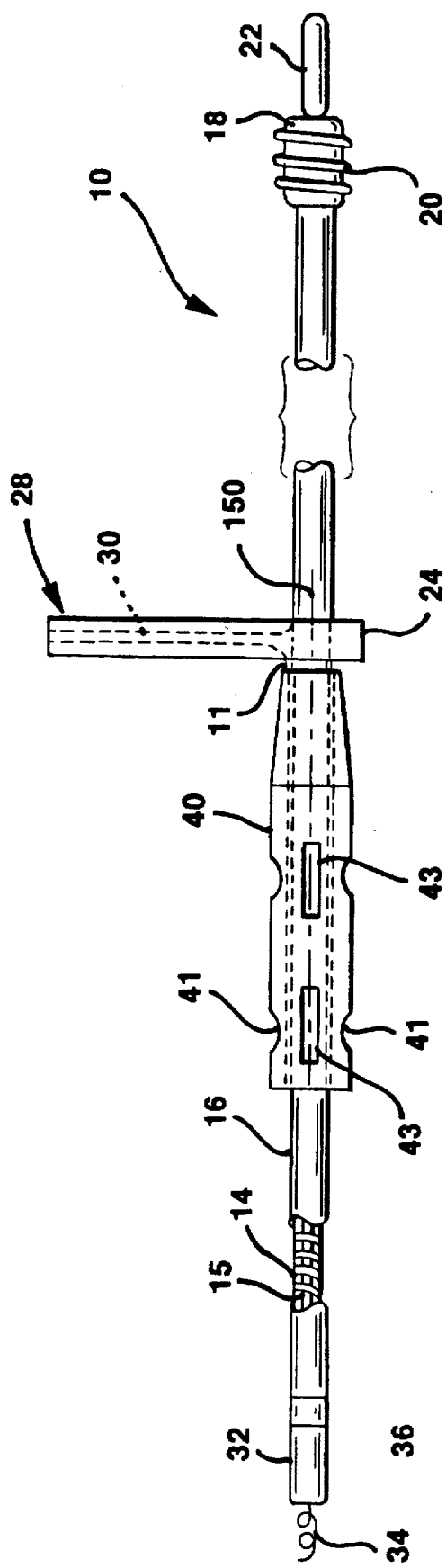
As seen in FIG. 1, the isodiametric transvenous lead 10 of the present invention may be constructed in any suitable fashion. As seen lead 10 is constructed through insulative sleeve 16 and outer conductor 14, shown here in cutaway portion. Outer conductor 14, in turn, itself encloses an inner insulative sleeve and an inner conductor, depicted generally by a hidden line 15. Conductors are preferably configured as concentric multi-filar coils of any suitable alloy, such as MP35N. Insulative sleeves may be fabricated of any flexible bio-compatible and bio-stable insulator. In the preferred embodiment silicone is used.

With continued reference to FIG. 1, an electrode and fixation assembly designated generally as 32 is disposed at the distal end of lead 10. Electrode and fixation assembly 32 is, in the disclosed embodiment, of the bipolar type and has tip electrode 34 at its distal end and a ring electrode 36 spaced proximally back from the distal end. Central imaginary axis 150 extends and is centered axially through the center of anchoring sleeve 40 and lead 10.

Anchoring sleeve 40 is positioned about lead 10 and serves as a point for suturing lead 10 to the tissue at the insertion point of the lead into the vein or tissue.

To attach anchoring sleeve 40 to the tissue, sutures are employed about suturing grooves 41 to squeeze or cinch anchoring sleeve 40 to the lead. Upon suturing the anchoring sleeve, slots 43 which are longitudinal to anchoring sleeve 40 and perpendicular to suturing grooves 41, enhance the suturing of the anchoring sleeve 40 to lead 10 by permitting anchoring sleeve 40 to be compressed and frictionally engage lead 10. After anchoring sleeve 40 has been secured to the lead, a few more sutures, as known in the art, are used about suturing grooves 41 to include tissue to affix lead 10 into position.

Anchoring sleeve 40, and terminal assembly 18 may be fabricated of any flexible bio-compatible and bio-stable material. In the preferred embodiment, the anchoring sleeve and the terminal assembly are fabricated from silicone. As discussed above, lead 10 and in particular anchoring sleeve 40 features anchoring sleeve retaining device 24.

FIG. 3 shows a cross section of anchoring sleeve 40 and lead 10 in phantom. Anchoring sleeve 40 has a lumen with a first diameter 140 greater than an outer diameter of lead 10, and a second diameter 124 which is less than the outer diameter of lead 10. Second diameter 124 may also be equal to the outer diameter of lead 10.

FIG. 4 is an alternative embodiment of the anchoring sleeve 40. As seen anchoring sleeve 40 is similar to that of FIG. 3, but for the fact that second diameter 124 is equal to the outer diameter of lead 10.

As can be appreciated by one skilled in the art, the narrowed portion of the lumen at second diameter 124 causes anchoring sleeve 40 to physically engage lead 10. Thus, the frictional properties of the material selected (silicone is preferred), will help prevent anchoring sleeve 40 from sliding along the lead or sliding off the distal end of the lead until implantation of the lead.

Figure 2:
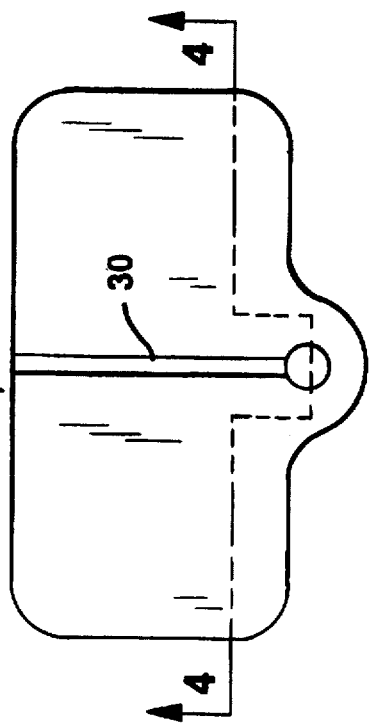

To remove retaining device 24 from anchoring sleeve 40, a scored tear 30 is provided along the second portion 24, with tabs 28, as shown in FIG. 2. The scored tear line will aid the physician in the removal of retaining device 24 along scored tear line 30 and through segment 11 of anchoring sleeve 40. After the retaining device has been removed, anchoring sleeve 40 may be moved into the proper position and the lead may be sutured into position.

Figure 5:
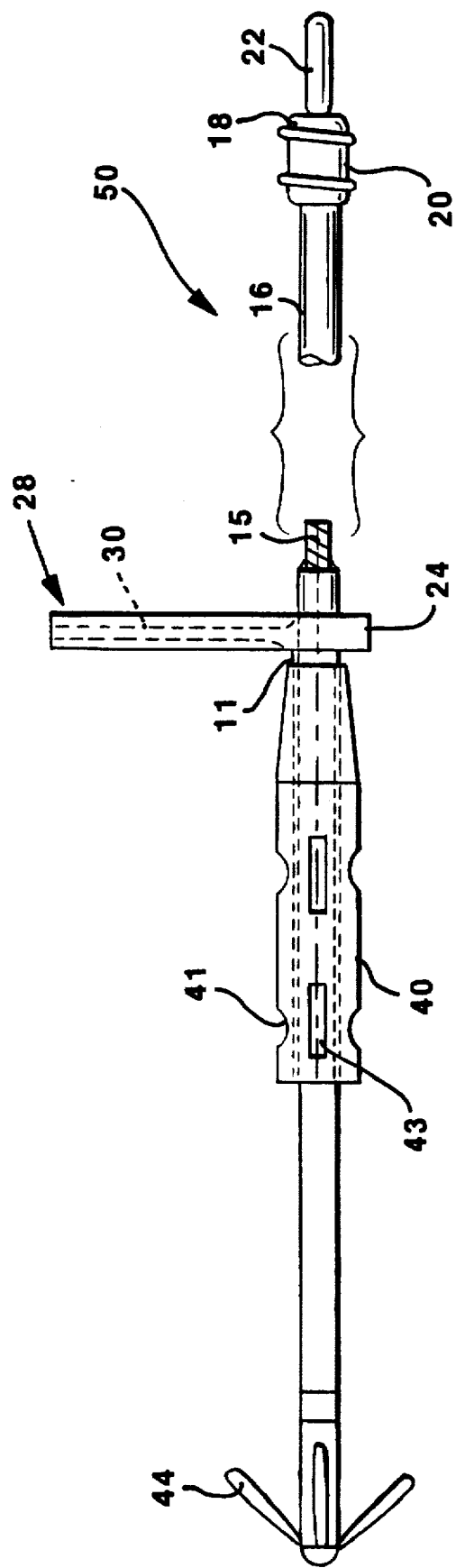

FIG. 5 shows a side plan view of an isodiametric lead 50 similar to the lead depicted in FIG. 1. However, lead 50 has a passive fixation mechanism in the form of tines 44.

Although two embodiments of the invention have been disclosed, this is done for purposes of illustration only and is not intended to be limiting with regard to the scope of the invention. It is to be contemplated that various substitutions, alterations, and/or modifications may be made to the disclosed embodiment without departing from the spirit and scope of the invention as defined in the following claims.

What is claimed is:

1. A body implantable lead, comprising:

a conductor having a proximal end and a distal end;

an insulating sleeve having an outer diameter, the insulating sleeve covering the conductor between the proximal end and the distal end;

an electrode coupled to the distal end of the conductor;

an electrical connector coupled to the proximal end of the conductor;

an anchoring sleeve positioned about the insulating sleeve and between the connector and the electrode, the anchoring sleeve having proximal and distal ends, the anchoring sleeve having a first lumen for accepting the conductor an insulting sleeve therewithin, the first lumen having an imaginary axis extending and centered axially therethrough, the first lumen having a first portion having a first diameter greater than the outer diameter of the insulating sleeve and a second portion having a second diameter less than the outer diameter of the insulating sleeve, the second portion being disposed at the proximal end of the anchoring sleeve and forming a manually tearable, thinned segment; and an anchoring sleeve retaining device having distal and proximal ends and a second lumen for accepting the conductor and insulating sleeve therewithin, the second lumen being disposed at least partially within a retaining device body and being aligned axially in respect of the first lumen and the imaginary axis, the retaining device having substantially parallel proximal and distal surfaces that project outwardly away from the central axis and the retaining device body, the surfaces terminating in a common outer edge, the distal end of the retaining device being attached by the thinned segment to the proximal end of the anchoring sleeve, a manually tearable scored tear line extending between the distal and proximal surfaces and from the outer edge to a location propinquant to the thinned segment.

2. A body implantable lead according to claim 1, wherein the first and second portions are constructed of silicone.

3. A body implantable lead according to claim 1, wherein the electrode comprises a tine fixation assembly.

4. A body implantable lead according to claim 1, wherein the lead is isodiametric.

5. A body implantable lead according to claim 1, wherein the anchoring sleeve further having at least one slot disposed therein, the slot extending between the first lumen and the outer surface of the anchoring sleeve.

6. A body implantable lead according to claim 1, wherein the anchoring sleeve further includes at least one suturing groove formed on the outer surface thereof.

7. A body implantable lead, comprising:

a conductor having a proximal end and a distal end; an insulating sleeve having an outer diameter, the insulating sleeve covering the conductor between the proximal end and the distal end;

an electrode coupled to the distal end of the conductor;

an electrical connector coupled to the proximal end of the conductor;

an anchoring sleeve positioned about the insulating sleeve and between the connector and the electrode, the anchoring sleeve having proximal and distal ends, the anchoring sleeve having a first lumen for accepting the conductor and sleeve therewithin, the first lumen having a first portion having a first diameter greater than the outer diameter of the insulating sleeve and a second portion having a second diameter less than the outer diameter of the insulating sleeve, the second portion being disposed at the proximal end of the anchoring sleeve and forming a manually tearable, thinned segment; and means for manually removing, at the location of the thinned segment, the second portion from the first portion, the removing means having distal and proximal ends and a second lumen for accepting the conductor and insulating sleeve therewithin, the distal end of the removing means being attached by the thinned segment to the proximal end of the anchoring sleeve.

8. An anchoring sleeve suitable for use in conjunction with a body implantable lead, where the lead has at least one inner conductor covered by an outer insulative sleeve, the anchoring sleeve accepting and gripping the lead therein, comprising:

a proximal end;

a distal end;

a first lumen for accepting the conductor and insulating sleeve therewithin, the first lumen having an imaginary axis extending and centered axially therethrough, the first lumen having a first portion having a first diameter greater than the outer diameter of the insulating sleeve and a second portion having a second diameter less than the outer diameter of the insulating sleeve, the second portion being disposed at the proximal end of the anchoring sleeve and forming a manually tearable, thinned segment; and an anchoring sleeve retaining device having distal and proximal ends and a second lumen for accepting the conductor and insulating sleeve therewithin, the second lumen being disposed at least partially within a retaining device body and being aligned axially in respect of the first lumen and the imaginary axis, the retaining device having substantially parallel proximal and distal surfaces that project outwardly away from the central axis and the retaining device body, the surfaces terminating in a common outer edge, the distal end of the retaining device being attached by the thinned segment to the proximal end of the anchoring sleeve, a manually tearable scored tear line extending between the distal and proximal surfaces and from the outer edge to a location propinquant to the thinned segment.

9. The anchoring sleeve of claim 8, wherein the anchoring sleeve is formed of silicone.

10. An anchoring sleeve according to claim 8, wherein the anchoring sleeve further includes at least one suturing groove formed on the outer surface thereof.

11. An anchoring sleeve according to claim 8, wherein the anchoring sleeve further has at least one slot disposed therein, the slot extending between the first lumen and the outer surface of the anchoring sleeve.

* * * * *

UNITED STATES PATENT AND TRADEMARK OFFICE
CERTIFICATE OF CORRECTION

PATENT NO. : 5,683,446

DATED : Nov. 4, 1997

INVENTOR(S) : James T. Gates

It is certified that error appears in the above-identified patent and that said Letters Patent is hereby corrected as shown below:

C. 3 L. 66   "conductor an" to be changed to "conductor and"

Signed and Sealed this

Twenty-third Day of November, 1999

Attest:

Q. TODD DICKINSON

*Attesting Officer*   *Acting Commissioner of Patents and Trademarks*